United States Patent [19]

Bluhm

[11] 4,083,965
[45] Apr. 11, 1978

[54] METHOD OF AND COMPOSITION FOR RELIEVING ITCH, PAIN AND SWELLING RESULTING FROM INSECT STINGS AND BITES AND SKIN CONTACT WITH NOXIOUS PLANTS

[76] Inventor: Henry P. Bluhm, Box 6538, Buena Park, Calif. 90620

[21] Appl. No.: 712,913

[22] Filed: Aug. 9, 1976

Related U.S. Application Data

[63] Continuation-in-part of Ser. No. 541,657, Jan. 16, 1975, abandoned.

[51] Int. Cl.² .............................................. A61K 33/42
[52] U.S. Cl. ..................................... 424/128; 424/127; 424/180; 424/310; 424/343; 424/357; 424/361
[58] Field of Search ................ 424/128, 180, 127, 361

[56] References Cited
PUBLICATIONS

Remington's Pharmaceutical Sciences, (1965), pp. 916–917, 1122–1123, 1442, 1445.

Webster's New World Dictionary, College Edition, 1966, p. 82.
The Dispensatory of the United States of America (21st Edition), p. 1374–1375.
British Pharmaceutical Codex, 1959, pp. 56–57.
Handbook of Non Prescription Drugs, (1973), pp. 190–194.

*Primary Examiner*—Leonard Schenkman
*Attorney, Agent, or Firm*—Mallinckrodt & Mallinckrodt

[57] ABSTRACT

A method of relieving itch, pain, and swelling resulting from insect stings, insect bites, and areas of skin contact with noxious plants, comprises topically applying to the affected area a composition containing at least either arrowroot, a calcium phosphate or a combination of both, as an active absorbent ingredient. A topical composition for use in the method comprises an active absorbent ingredient selected from the group thereof consisting of arrowroot, a calcium phosphate and a mixture thereof; and a carrier suitable for topical application to the human skin.

8 Claims, No Drawings

METHOD OF AND COMPOSITION FOR RELIEVING ITCH, PAIN AND SWELLING RESULTING FROM INSECT STINGS AND BITES AND SKIN CONTACT WITH NOXIOUS PLANTS

RELATED APPLICATIONS

This application is a continuation-in-part of my copending application Ser. No. 541,657 filed Jan. 16, 1975 now abandoned.

BACKGROUND OF THE INVENTION

1. Field

This invention is in the field of non-prescription topical compositions for treatment of allergenic effects such as itching, pain, and swelling resulting from insect stings and bites and areas of skin contact with noxious plants.

2. State of the Art

There are numerous preparations presently available to provide relief from the allergenic effects of insect stings and bites or for relief from the effects of contact of the skin with noxious plants. Most of these preparations are effective only to a degree and merely tend to anesthetize the site of the affected area. There is nothing that tends to draw the actual material causing the allergenic reaction from the site.

It is said that the Indians in Central America used arrowroot (a starch taken from the root of a plant) in the treatment of poison arrow wounds and that that is how it received its name. Although arrowroot is presently used as a starch in cooking, it appears to have no significant medicinal uses.

SUMMARY OF THE INVENTION

According to the invention, a method of relieving the allergenic effects of insect stings, insect bites, and areas of skin contact with noxious plants, comprises topically applying to the affected area a composition containing at least either arrowroot, a calcium phosphate, or a combination of them both, as an active absorbent ingredient.

A composition for topical use in accordance with the method comprises an active absorbent ingredient as above indicated in a carrier suitable for topical application to the human skin, for example, in a mixture of glycerine and water.

It has been found that an active absorbent ingredient as noted above works very well to alleviate the allergenic effects of insect stings and bites and areas of skin contact with noxious plants. Although either arrowroot or a calcium phosphate alone works satisfactorily, combinations of the two, or combinations of either with pumice work much more rapidly than does the arrowroot or calcium phosphate alone. The remainder of the composition may comprise carriers, emulsifiers, and/or dispersants and may take the form of a powder, liquid, or paste. The composition is preferably made in the form of a cream or lotion for application directly to the skin at the affected site.

When applied to insect stings or bites or areas of skin contact with noxious plants, it appears that the active ingredient actually draws the allergenic or poisonous substance from the affected area along with any body materials resulting from swelling or infection. The treatment has also been found effective in removing skin blemishes such as pimples and blackheads.

If desired, a mild anesthetic, such as menthol, chloroform, or benzocaine, or an antibiotic may be included in the composition.

DETAILED DESCRIPTION OF THE PRESENTLY PREFERRED EMBODIMENTS

It has been found that very effective relief from the allergenic effects of insect stings, insect bites, and areas of skin contact with noxious plants may be had by topically applying to the affected area a composition containing at least either arrowroot, a calcium phosphate, or a combination of both, as an active absorbent ingredient. Not only is the itching relieved, but any attendant swelling that has occurred is removed, and further swelling, itching or other allergenic effects are prevented.

While satisfactory relief is obtained by applying either arrowroot or a calcium phosphate alone as the active absorbent ingredient, the combination of arrowroot with a calcium phosphate, or either arrowroot or a calcium phosphate with pumice, has been found to produce a synergistic effect which unexpectedly relieves the allergenic effects much more rapidly than either the arrowroot or calcium phosphate acting alone. The combination usually offers effective relief within less than a minute if applied shortly after the sting or bite occurs.

A composition of the preferred character contains, as an active ingredient, an absorbent comprising either arrowroot, a calcium phosphate, a mixture of arrowroot and one or more calcium phosphates, a mixture of arrowroot and one or more calcium phosphates, a mixture of arrowroot and pumice, a mixture of arrowroot, pumice, and one or more calcium phosphates, or a mixture of one or more calcium phosphates and pumice. The calcium phosphate used is preferably either di-calcium phosphate or tri-calcium phosphate or a mixture of the two.

It is believed that the active absorbent ingredient operates to draw the acids, mucoids, poisons, and debris from the site of the bite, sting, or area of skin contact with the noxious plants. These acids, mucoids, poisons, and debris are then absorbed, neutralized and diluted in the composition and are later rinsed away with the composition.

In addition to the active absorbent ingredient, it is preferred that the composition also comprise sodium lauryl sulfate, sodium N-lauroyl sarcosinate or other detersives as carriers and cleaning agents and to improve skin adhesion when in a wet state; humectants such as glycerin, sorbital, propylene glycol, or other polyhydric alcohols to avoid drying; binders and emulsifiers such as sodium ricinoleate, the natural gums tragacanth, karaya, arabic, the algenates, and Irish Moss, and the water soluble salts of cellulose ethers, such as sodium carboxymethyl cellulose and sodium carboxymethyl hydroethyl cellulose; an opactifier such as titanium dioxide; and water as a solvent. Dimethecone may be used as a binder and thickener, and sodium benzoate and magnesium aluminum silicate may be used as texturizers.

In some instances it may be desirable to add a mild anesthetic such as chloroform, menthol, or benzocaine, or to add an antibiotic, to the composition.

It is preferred that the composition be in the form of a cream or lotion for easy application and adhesion to the affected area, although a composition in other forms, such as powder, could be used. If stored in powdered form, a small amount of water can be mixed with the powdered composition before use to improve the adhesive qualities.

The maximum concentration of the active ingredient is limited only by the desired form and consistency of the composition. Active ingredient concentrations of over 80% may be used while still obtaining a satisfactory cream consistency. The preferred range of concentration of the active ingredient from the standpoint of fast action, absorption capacity, and cosmetic quality of the composition as a cream, is between 15 and 80%. At low concentrations of the active ingredient the composition acts more slowly and has smaller absorption capacity. The composition appears to work well down to about 5% or less active ingredient concentration particularly for small bites or stings.

An example of a formulation of the composition that has been used, given in weight percentages, is:

| Arrowroot | 5 – 20% |
|---|---|
| Pumice | 10 – 23% |
| Sodium benzoate | 0.08% |
| Hydrochloride of guanidino benzimidazole | 0.25% |
| Insoluble sodium metaphosphate | 20.30% |
| Sodium N-lauroyl sarcosinate | 1% |
| Dicalcium phosphate | 2.15% |
| Titanium dioxide | 0.20% |
| Tragacanth | 0.7% |
| Glycerine | 32% |
| Water (distilled) | balance |

Indications are that the hydrochloride of guanidino benzimidazole which was used as an absorbent filler ingredient, as is the insoluble sodium metaphosphate, may be toxic so is no longer recommended for use. In its place it is preferred that a silica gel be used.

A presently preferred formulation is:

| Arrowroot | 28% |
|---|---|
| Pumice | 20% |
| Sodium lauryl sulfate | 30% |
| Titanium dioxide | 1% |
| Sodium ricinoleate | 2% |
| Glycerine and water | 16% |
| Tragacanth | 1% |
| Menthol | 2% | with an alternate preferred formulation being:

| Arrowroot | 28% |
|---|---|
| Pumice | 5% |
| Tricalcium phosphate | 4% |
| Dicalcium phosphate | 35% |
| Magensium aluminum silicate | 0.8% |
| Sodium lauryl sulfate | 1.5% |
| Titanium dioxide | 1.5% |
| Sodium carboxymethyl cellulose | 1.2% |
| Dimenthecone | 1.5% |
| Menthol | 3% |
| Irish Moss | 0.5% |
| Glycerine | 21.5% |
| Water | to the desired consistency |

All of the ingredients are preferably in the form of powder before mixing except glycerine and water, and the other humectants that may be used, which are liquids. Some forms of silica gel may also be liquid.

Arrowroot is commercially available in most supermarkets and is distributed under that name by McCormick & Co., (Schilling) Baltimore, Maryland. The remaining ingredients are availble from normal chemical outlets such as McKesson Chemical Company, Irvine, California, or Sargent Welch Company, Anaheim, California.

In actual use to treat insect stings and bites, when the composition is applied to the site soon after the sting or bite occurs, effective relief is had in a manner of seconds. In a case of extreme reaction to mosquito bites where welts as large as dollars and raised above the skin in irregular patterns were treated with the composition 12 hours after the bites occurred, all swelling and allergenic reactions were gone after 3½ hours.

In instances of severe allergenic effects to stings and bites, it is important to apply the composition immediately after the sting or bite is received so that the allergenic material can be withdrawn rapidly from the body before it can get into the bloodstream.

The composition has also been found to be very effective for the treatment and removal of skin blemishes such as pimples and blackheads. Pimples have disappeared within three hours of application. Blackheads are loosened by the absorption of the surrounding oils and waxes and may then be washed away.

Whereas the invention has been described herein with reference to the presently preferred composition thereof, it should be understood that various changes may be made without departing from the disclosed inventive concepts particularly pointed out and claimed hereinafter.

I claim:

1. A method of relieving the itch, pain, and swelling resulting from insect stings, insect bites, and skin contact with noxious plants, comprising topically applying to the affected area a composition containing an effective amount of an active ingredient selected from the group consisting of one or more calcium phosphates; arrowroot; a mixture of arrowroot and one or more calcium phosphates; a mixture of arrowroot and pumice; a mixture of arrowroot, pumice, and one or more calcium phosphates; and a mixture of one or more calcium phosphates and pumice; together with a carrier material for said active ingredient.

2. A composition for topical application to the site of insect stings, insect bites, and areas of skin contact with noxious plants to relieve the itch, pain, and swelling associated therewith, comprising an effective amount of an active ingredient selected from the group thereof consisting of a mixture of arrowroot and one or more calcium phosphates; a mixture of arrowroot and pumice; a mixture of arrowroot, pumice, and one or more calcium phosphates; and a mixture of one or more calcium phosphates and pumice; and a carrier for said active ingredient suitable for topical application to the human skin.

3. A composition for topical application according to claim 2, wherein the calcium phosphates is dicalcium phosphate or tricalcium phosphate.

4. A composition for topical application according to claim 2, wherein the active ingredient comprises at least 5% by weight of the composition.

5. A composition for topical application according to claim 2, wherein the active ingredient comprises between 15 and 80% by weight of the composition.

6. A composition for topical application according to claim 2, in the form of a cream.

7. A composition for topical application according to claim 2, wherein the composition additionally includes an anesthetic.

8. A composition for topical application according to claim 7, wherein the anesthetic is selected from the group consisting of menthol and benzocaine.

* * * * *